(12) United States Patent
Tsoref

(10) Patent No.: US 7,204,807 B2
(45) Date of Patent: Apr. 17, 2007

(54) JOINT ANALYSIS USING ULTRASOUND

(75) Inventor: Liat Tsoref, Tel-Aviv (IL)

(73) Assignee: Sunlight Medical Ltd., Tel-Aviv (IL)

( * ) Notice: Subject to any disclaimer, the term of this patent is extended or adjusted under 35 U.S.C. 154(b) by 141 days.

(21) Appl. No.: 10/484,403

(22) PCT Filed: Aug. 16, 2001

(86) PCT No.: PCT/IL01/00763

§ 371 (c)(1),
(2), (4) Date: Jan. 21, 2004

(87) PCT Pub. No.: WO03/009762

PCT Pub. Date: Feb. 6, 2003

(65) Prior Publication Data

US 2004/0193048 A1    Sep. 30, 2004

(30) Foreign Application Priority Data

Jul. 24, 2001    (WO) ................. PCT/IL01/00683

(51) Int. Cl.
*A61B 8/00*    (2006.01)
(52) U.S. Cl. .................. 600/438; 600/443; 382/128
(58) Field of Classification Search ........ 600/437–449, 600/458; 128/916; 73/625–626; 382/128, 382/258, 263, 266, 274
See application file for complete search history.

(56) References Cited

U.S. PATENT DOCUMENTS

| | | | |
|---|---|---|---|
| 5,197,475 A | 3/1993 | Antich et al. | |
| 5,487,388 A | 1/1996 | Rello et al. | |
| 5,509,042 A | 4/1996 | Mazess | |
| 5,532,169 A | 7/1996 | Eyre | |
| 5,533,519 A | 7/1996 | Radke et al. | |
| 5,564,423 A | 10/1996 | Mele et al. | |
| 5,577,089 A | 11/1996 | Mazess | |
| 5,605,155 A | 2/1997 | Chalana et al. | |
| 5,605,156 A | 2/1997 | Drzewiecki et al. | |
| 5,651,363 A | 7/1997 | Kaufman et al. | |
| 5,704,356 A | 1/1998 | Shmueli | |
| 5,806,520 A | 9/1998 | Berger et al. | |
| 5,824,085 A * | 10/1998 | Sahay et al. ................. 128/898 |
| 5,895,364 A | 4/1999 | Donskoy | |
| 6,035,227 A | 3/2000 | Shmueli | |

(Continued)

FOREIGN PATENT DOCUMENTS

| | | |
|---|---|---|
| EP | 0 341 969 | 11/1989 |
| EP | 0 626 656 | 11/1994 |
| EP | 0 797 952 | 10/1997 |
| FR | 2 768 322 | 3/1999 |
| WO | WO 00/28316 | 6/2000 |

OTHER PUBLICATIONS

Gahunia, H.K. et al.; "Osteoarthritis Staging: Comparison between magnetic resonance imaging, gross pathology and histopathology in the rhesus macaque;" 1995; Osteoarthritis and Cartilage; vol. 3; pp. 169-180.

(Continued)

*Primary Examiner*—Francis J. Jaworski
(74) *Attorney, Agent, or Firm*—Fenster & Company

(57) ABSTRACT

A method is provided for generating at least one quantitative measure of a joint comprising sending an acoustic signal to at least a part of a joint, receiving said acoustic signal after modification by said joint, analyzing the received acoustic signal with a computer, and generating, from said computer, one or more of a quantitative surface, quantitative volumetric and quantitative measurements of the physical properties of the joint or a portion thereof.

47 Claims, 9 Drawing Sheets

U.S. PATENT DOCUMENTS

| | | | |
|---|---|---|---|
| 6,074,352 | A | 6/2000 | Hynynen et al. |
| 6,135,960 | A | 10/2000 | Holmberg |
| 6,160,866 | A | 12/2000 | Mazess et al. |
| 6,280,402 | B1 | 8/2001 | Ishibashi et al. |
| 6,306,089 | B1 | 10/2001 | Coleman et al. |
| 6,413,215 | B1 * | 7/2002 | Wu et al. ................. 600/437 |
| 6,454,712 | B1 | 9/2002 | Oomuki |
| 6,463,167 | B1 * | 10/2002 | Feldman et al. ............ 382/128 |
| 6,468,215 | B1 | 10/2002 | Sarvazyan et al. |
| 6,585,666 | B2 * | 7/2003 | Suh et al. ................. 600/587 |
| 6,607,487 | B2 * | 8/2003 | Chang et al. ............... 600/437 |
| 6,799,066 | B2 * | 9/2004 | Steines et al. .............. 600/407 |
| 6,836,557 | B2 * | 12/2004 | Tamez-Pena et al. ....... 382/128 |
| 2002/0162031 | A1 | 10/2002 | Levin et al. |
| 2003/0035773 | A1 * | 2/2003 | Totterman et al. ........... 424/9.1 |
| 2003/0055502 | A1 * | 3/2003 | Lang et al. .............. 623/16.11 |
| 2003/0229299 | A1 * | 12/2003 | Shimura et al. ............ 600/595 |

OTHER PUBLICATIONS

Gonzalez, R.C. et al.; "Digital Image Processing;" 1992; Addison-Wesley Publishing Company; New York; USA; pp. 506-518.

Haralick, R. et al.; "Textural Features for Image Classification;" Nov. 1973; IEEE Transactions on Systems, Man, and Cybernetics.; vol. SMC-3, No. 6; pp. 610-621.

Jain, A.K.; "Fundamentals of Digital Image Processing;" 1989; Prentice-Hall; Englewood Cliffs; NJ; USA; pp. 313-331, 394-400.

Lequin, M.H. et al.; "Normal Values for Tibial Quantitative Ultrasonometry in Caucasian Children and Adolescents (Aged 6 to 19 Years);" 2000; Calcified Tissue International; vol. 67; pp. 101-105.

Vince, D.G. et al; "Comparison of texture analysis methods for the characterization of coronary plaques in intravascular ultrasound images;" 2000; Computerized Medical Imaging and Graphics; vol. 24; pp. 221-229.

Adler, R. S. et al.; "Quantitative Assessment of Cartilage Surface roughness in Osteoarthritis Using High Frequency Ultrasound;" 1992; Ultrasound in Medicine and Biology; vol. 18, No. 1; pp. 51-58; UK; XP008004715.

Aisen, A. M. et al.; "Sonographic Evaluation of the Cartilage of the Knee;" Dec. 1983; Radiology; vol. 153, No. 3; pp. 781-784.

Castriota-Scanderbeg, A. et al.; "Skeletal Age Assessment in Children and Young Adults: Comparison Between a Newly Developed Sonographic Method and Conventional Methods;" 1998; Skeletal Radiology; vol. 27; pp. 271-277.

Grassi, W. et al.; "Sonographic Imaging of Normal and Osteoarthritic Cartilage;" Jun. 1999; Seminars in Arthritis and Rheumatism; vol. 28, No. 6; pp. 388-403.

Iagnocco, A. et al.; "Sonographic Evaluation of Femoral Condylar Cartilage in Osteoarthritis and Rheumatoid Arthritis;" 1992; Scand. J. Reumatol.; vol. 21; pp. 201-203.

Lefebvre, F. et al.; "Automatic Three-Dimensional Reconstruction and Characterization of Articular Cartilage from High-Resolution Ultrasound Acquisitions;" Dec. 1998; Ultrasound in Medicine and Biology; vol. 24, No. 9; pp. 1369-1381; New York, NY; US; XP004295291.

McCune, W. J. et al.; "Sonographic Evaluation of Osteoarthritic Femoral Condylar Cartilage;" May 1990; Clinical Orthopaedics and Related Research; No. 254; pp. 230-235.

Mughal, M. Z., et al.; "Assessment of Bone Status in Children Using Quantitative Ultrasound Techniques;" 1999; Quantitative Ultrasound: Assessment of Osteoporosis and Bone Status; Chapter 17; pp. 309-323; Edited by Njeh, C. F. et al.

Roches, A. F. et al.; "The RWT Method for the Prediction of Adult Stature;" Dec. 6, 1975; Pediatrics; vol. 56; No. 6; pp. 1026-1033.

Sun, Y. N. et al.; "A Computer System for Skeletal Growth Measurement;" 1994; Computers and Biomedical Research; vol. 27; pp. 2-12; XP002067754.

Tanner, J. M. et al.; "Prediction of Adult Height from Height, Bone Age, and Occurrence of Menarche, at Ages 4 to 16 with Allowance for Midparent Height;" 1975; Archives of Disease in Childhood; vol. 50; pp. 14-26.

Tanner, J. M. et al.; "Prediction of Adult Height from Height and Bone Age in Childhood;" 1983; Archives of Disease in Childhood; vol. 58; pp. 767-776.

Todd, T. W.; "Age Changes in the Pubic Bone;" Jul.-Sep. 1920; American Journal of Physical Anthropology; vol. 3, No. 3; pp. 285-334.

Todd, T. W. et al.; "Endocranial Suture Closure, its Progress and Age Relationship;" 1924; American Journal of Physical Anthropology; vol. 7; pp. 325-384.

Tomlinson, J. E. et al.; "Ultrasonographic Evaluation of Tarsocrural Joint Cartilage in Normal Adult Horses;" 2000; Veterinary Radiology and Ultrasound; vol. 41, No. 5; pp. 457-460.

Van Den Hoogen, B. M. et al.; "Effect of Exercise on The Proteoglycan Metabolism of Articular Cartilage in Growing Foals;" 1999; Osteochondrosis and Musculoskeletal Development; Equine vet. J. Sappl.; vol. 31; pp. 62-66.

Wear, K. A. et al.; "Assessment of Bone Density Using Ultrasonic Backscatter;" Jun. 1998; Ultrasound Med. Biol.; vol. 24, No. 5; pp. 689-695.

Wilson, A. et al.; "Development of Automated Ultrasonic Measurements of Articular Cartilage Thickness and Surface Morphology;" Oct. 28-31, 1993; Biomechanics, Rehabilitation, Electrical Phenomena, Biomaterials; San Diego; Proceeding of the Annual International Conference of the Engineering in Medicine and Biology Society; vol. 3, Conf. 15; pp. 1122-1123; New York; IEEE; US; XP000452803.

* cited by examiner

| SECTOR | | CT | P | PA | CPD | WCV | CVP | CCV |
|---|---|---|---|---|---|---|---|---|
| 554 | E | 1.2 | 4 | .85 | .6 | 122 | .510 | 121.49 |
| 558 | D | 2.2 | 0 | 0 | 0 | 142 | 0 | 142 |
| 560 | E | 1.3 | 2 | 1.1 | .62 | 136 | .682 | 135.58 |
| 560 | F | 1.4 | 1 | 1.35 | 1.39 | 139 | .65 | 138.35 |

| CT | CARTILAGE THICKNES mm |
|---|---|
| P | NUMBER OF PITS |
| PA | SQUARE AREA OF PITS mm$^2$ |
| CPD | CARTILAGE PIT DEPTH mm |
| TCV | WHOLE CARTILAGE VOLUME mm$^3$ |
| CVP | CUBIC VOLUME OF PITTING mm$^3$ |
| CCV | CARTILAGE CUBIC VOLUME mm$^3$ |

JOINT ANALYSIS USING ULTRASOUND

RELATED APPLICATIONS

The present application is a US National Phase of PCT. Application No. PCT/IL01/00763, filed on Aug. 16, 2001.

FIELD OF THE INVENTION

The present invention relates to quantifying joint measurements using ultrasound.

BACKGROUND OF INVENTION

Observation of joint structures with ultrasound, though described in many articles in the past decades, has failed to become an accepted joint measurement tool. As early as 1983, ultrasound was suggested as a means of observing joint cartilage. As an example, Alex M. Aisen, MD et. al. *Radiology* Vol. 153 Number 3, December 1983, "Sonographic Evaluation of the Cartilage of the Knee," demonstrates the use of ultrasound in observing "changes in the surface characteristics and thickness of cartilage". This ultrasound method relies on subjectively evaluating an ultrasound image.

Ultrasound has the potential to be useful in observing some joint structures besides cartilage. According to Iagnocco, et al. *Scand. J Rheumatol* Vol. 21: 201–203, 1992 in "Sonographic Evaluation of Femoral condylar Cartilage in osteoarthritis and rheumatoid arthritis," "Sonography of the knee makes it possible to study the anatomical details of this articulation such as synovial membrane, intra-articular fluid, articular cartilage, ligaments and tendons, menisci, possible popliteal cysts, their dimensions and location." Again, this ultrasound method relies on subjective evaluation of an ultrasound image.

Allessandro Castriota-Scanderbeg et al., in "Skeletal age assessment in children and young adults: Comparison between a newly developed sonographic method and conventional methods," Skeletal Radiology 1998 27:271–277, propose a method for assessing skeletal age using ultrasound imaging measurements of the thickness of femoral head articular cartilage.

Ultrasound can also provide important information about horse joint conditions that is important to their trainers, as stated by Tomlinson BVSc., et. al., *Veterinary Radiology and Ultrasound* Vol. 41 no. 5, 2000 pp. 457–460 "Ultrasonographic evaluation of Tarsocrural Joint Cartilage in Normal Adult Horses," "Diagnostic ultrasound has proven to be more sensitive than radiology for the early identification of periarticular remodeling and osteophyte formation" in evaluating equine Osteoarthritis. Again, this method relies on subjective evaluation of an overall ultrasound image.

Ultrasound observation of joint structures is advantageous because its probes can be applied external to the body so it can be used in a non-sterile environment. Ultrasound provides joint inspection without using ionizing radiation as does X-ray, allowing examinations to be repeated frequently without risk to the patient. Ultrasound does not require a special media, such as an X-ray plate, with which to gather data and can provide better resolution than X-ray, particularly of the cartilage and soft tissue structures. Also, ultrasound is a less expensive imaging unit than X-ray, CT or MRI. For these reasons, ultrasound is useful for imaging in a doctor's office, mobile clinics, theater of battle or in screening programs in undeveloped countries.

Yet, for all its advantages, ultrasound has not lived up to its potential. As noted by Walter Grassi et al., June 1999 *Seminars in Arthritis and Rheumatism* vol. 29, No. 6. "Sonographic Imaging of Normal and Osteoarthritic Cartilage," as of mid-1999, ultrasound potential "is still under investigation."

Ultrasound has apparently not gained widespread use for assessing joints beyond imaging, in spite of its apparent suitability.

Overview of Joint Structures

Joints are connections, typically movable, between two or more bones and include many structures that lend themselves to quantitative measurement. Such structures include, but are not limited to cartilage, chondrocytes, subchondral bone, joint capsule, joint fluid, ligaments and tendons:

(a) Cartilage is a tissue that consists of cells called chondrocytes in an extracellular matrix. The cartilage coats the ends of bones within a joint. Cartilage acts as a shock absorber against impact to the ends of bone during actions such as walking, running or jumping. The surface of cartilage provides an almost friction-free surface between bones as they move against each other.

(b) Chondrocytes are cells that lay down new cartilage. Chondrocytes produce and maintain the extracellular matrix.

(c) Subchondral bone, is a part of the bone that is located directly below cartilage and demonstrates changes in a variety of states that affect a joint.

(d) Joint fluid is a complex liquid that serves to nourish the cartilage, lubricate the tissue of a joint and carry waste away from cartilage.

(e) Joint capsule is a flexible tissue joint covering that gives a joint support and seals in the joint fluid that lubricates the joint structures. Its inner lining is the synovial membrane that produces and replenishes joint fluid.

(f) Ligaments are fibrous bands that connect one bone to another, usually within or part of a joint capsule.

(g) Tendons are the fibrous ends of a muscle that attaches it to bone and can be incorporated into joint structures.

SUMMARY OF THE INVENTION

An aspect of some embodiments of the invention relates to acquiring quantitative measures of joint properties, in particular, surface, physical and volumetric measures.

As used herein the term quantitative surface measure means a value that characterizes a property of a two dimensional surface measurement of at least a part of a joint structure, such as the amount of surface area affected by osteoarthritis-related pitting.

As used herein the term physical measure means a value that characterizes a property of internal volume of at least a part of a joint structure, such as cartilage. Exemplary physical measures include speed of sound, density of osteophytes and cross-sectional brightness.

As used herein the term volumetric measure means a value that characterizes the volume of at least a part of a joint structure, such as cartilage. An exemplary volumetric measure is the volume of an area of joint cartilage that has been affected by thinning and/or pitting due to osteoarthritis.

Being quantitative, rather than qualitative, such measures can be used, for example, to indicate a joint state directly, for example, in quantifying the quality of cartilage. In some exemplary embodiments of the invention, measures are generated on the basis of average, relative or other statistical properties and/or on the basis of absolute measurements of a joint.

In an exemplary embodiment of the present invention, quantitative ultrasound joint measurements are acquired during performance of different activities, for example during walking or running.

In an exemplary embodiment of the present invention, quantitative ultrasound joint measures are compiled into a database that associates a qualitative meaning or a state identification with raw measurement data. Such a database, for example, correlates ultrasound measurements with age, weight, occupation sex, ethnic group and/or related disease state.

An aspect of some embodiments of the invention relates to establishing quantitative joint properties of two or more regions of a joint structure. In one example, a quantitative comparison is made between the degree of pitting in two or more regions of cartilage. An exemplary use of such quantitative information is in locating optimal cartilage graft donor sites and optimal cartilage graft recipient sites in autogenous cartilage reconstruction.

An aspect of some embodiments of the invention is correlation of quantitative ultrasound joint measures with disease states. Osteoarthritis, for example, is a disease that results from overuse and/or improper use of a joint and often becomes manifest after repeated inflammation of a joint. In osteoarthritis, joint structures, such as cartilage, bone, subchondral bone, and soft tissue, can be quantitatively measured to provide an indication of disease. Such indication may lead, possibly in conjunction with other measures, to diagnosis and/or provide an indication for ongoing treatment regimen.

Additionally or alternatively, quantitative ultrasound joint measurements are correlated with disease state progression in genetic joint disease, such as in sarcoid. Optionally, quantitative measurements are used to track disease progression during treatment.

Additionally or alternatively, quantitative measures are correlated with other physiologic measurements, for example, blood value measurements. In an exemplary embodiment blood uric acid levels are correlated with joint cysts containing uric acid in hyperuricemia There is thus provided, in accordance with an embodiment of the invention, a method for generating at least one quantitative measure of a joint comprising sending an acoustic signal to at least a part of a joint;

receiving said acoustic signal after modification by said joint;

analyzing the received acoustic signal with a computer; and generating, from said computer, one or more of a quantitative surface, quantitative volumetric and quantitative measurements of the physical properties of the joint or a portion thereof.

In an embodiment of the invention, generating a quantitative measure comprises generating a value of a quantitative surface measure.

Optionally, generating a value of a surface quantitative measure comprises establishing a region of interest within a pixel image generated from said received acoustic signal and measuring the brightness of pixels within said region of interest.

Optionally, generating a value of a surface quantitative measure comprises establishing a region of interest within a pixel image generated from said received acoustic signal and averaging the brightness of pixels within said region of interest. Optionally, the region of interest is a line. Optionally, the region of interest is determined manually by an operator. Optionally, the method includes a computer automatically determining a region of interest.

In an embodiment of the invention, generating comprises generating a value of a quantitative volumetric measure from said acoustic signal. Optionally, the volumetric value comprises the amount or volume of one or more of pitting in cartilage, bone cysts, joint fluid, osteophytes.

In an embodiment of the invention, said generating is a quantitative physical measure from said acoustic signal. Optionally, said physical measure from said acoustic signal comprises one or more of acoustic velocity, acoustic backscatter or acoustic attenuation.

Optionally, receiving the acoustic signal comprises generating a pixel image from said joint.

Optionally, analyzing the received acoustic signal comprises establishing a region of interest within a pixel image generated from said received acoustic signal.

Optionally, the quantitative measure comprises two or more measurements. Optionally, the quantitative measure comprises two or more measurements taken at separate times. Optionally, the quantitative measure comprises two or more measurements taken from separate areas of said joint.

Optionally, the method includes comparing two or more measurements to each other.

Optionally, said quantitative measure comprises one or both of an echo method and through method.

Optionally said received acoustic signal comprises a global joint measure.

In an embodiment of the invention, the method includes activating the joint in conjunction with said sending and receiving. Optionally, said sending and receiving is performed during said activation. Optionally, sending and receiving is performed following said activation. Optionally, sending and receiving is performed prior to said activation.

In an embodiment of the invention, the method includes repeating said receiving, analyzing and generating values, for at least two different regions of said joint. Optionally, the method includes arranging said values for at least two different regions into a spatial map. Optionally, the method includes combining said values for at least two different regions into a qualitative descriptor.

In an embodiment of the invention, the method includes repeating said receiving, analyzing and generating values at least two different times for substantially the same measurement.

In an embodiment of the invention, the quantitative measure provides a measure of cartilage.

In an embodiment of the invention, the quantitative measure provides a measure of joint structures of one or more of synovial membrane, joint fluid, joint capsule, a ligament, a bone, a tendon and an osteophyte.

In an embodiment of the invention, the joint comprises one or more of a hip joint, a knee joint, an ankle joint, a tarsal joint, a metatarsal joint, a phalanx joint, a shoulder joint, an elbow joint and a wrist joint.

In an embodiment of the invention, the joint comprises at least one of a syndesmosis, a synchondrosis, a diarthrodial joint, a synostosis.

In an embodiment of the invention, the joint is an equine joint. Optionally, the joint is at least one of, an equine intertarsal joint, an equine tarso-metatarsal joint, and an equine metatarsal joint.

In an embodiment of the invention, the joint is a human joint.

Optionally, the acoustic signal is received from a receiver located outside of said joint. Optionally, the acoustic signal is received from a receiver located inside of said joint.

Optionally, the signal is transmitted from a transmitter located inside of said joint. Optionally, the signal is transmitted from a transmitter located outside of said joint.

In an embodiment of the invention, said analyzing comprises receiving said acoustic signal from said joint, generating a pixel image from said joint and averaging the brightness of pixels along at least one line of pixels from said image.

Optionally, generating comprises generating a value based on said average. Optionally, the at least one line comprises at least two lines. Optionally, the method comprises displaying averages of the brightness of pixels along two or more lines in graph format. Optionally, the graph displays averages of pixel brightness along two or more lines through one or more of a cartilage region, a bone region; and a non-cartilage soft tissue region. Optionally, a quantitative value is generated based on the amplitude of values of said averages of pixel brightness. Optionally, a quantitative value is generated based on the slope of said averages of pixel brightness.

In an embodiment of the invention, the measurement is responsive to a signal that passes through a joint structure.

In an embodiment of the invention, the measurement is responsive to a signal that echoes from a joint structure.

Optionally, the ultrasound signal provides a measure of one of; speed of sound, broadband ultrasound attenuation and dispersion of ultrasound signal.

Optionally, the method includes arranging said values into a spatial map. Optionally, the method includes arranging said generated values into a temporal map.

In an embodiment of the invention, the quantitative value is correlated with one or more qualitative descriptors based on one or more alternative joint measurement methods. Optionally, the method includes correlating at least two of said values with one of an MRI image of said joint, an X-ray CT or a nuclear scan image of said joint to provide a qualitative measure.

There is further provided, in accordance with an embodiment of the invention, a method of comparing at least one quantitative measurement to at least one qualitative descriptor, comprising:

acquiring one or more quantitative measurements from at least one joint;

correlating, using a computer, said one or more quantitative measurements with one or more qualitative descriptors; and generating a qualitative descriptor based upon said correlation.

In an embodiment of the invention, the one or more quantatative measurement s include measurements of cartilage.

Optionally, the qualitative descriptor comprises a clinical index of said joint.

Optionally, the qualitative descriptor comprises joint measures from one or more of an X-ray, an MRI image, an X-ray CT or a nuclear scan image.

Optionally, correlating comprises using a formula.

Optionally, correlating comprises using a formula with one or more of the slope of the cartilage-soft tissue margin, the slope of the cartilage-bone margin, the minimum of the cartilage brightness and the maximum of the bone brightness as it appears in a cross sectional brightness graph of ultrasound data,as parameters.

Optionally, the method includes associating one or more personal parameters with said one or more values in said database. Optionally, the personal parameters comprise one or more more of age, sex, ethnic group, sport preference, activity level, occupation, geographic location and nationality. Optionally, the personal parameters comprise one of joint disease symptoms, genetic joint disease inheritance, familial systemic disease, blood values, infectious disease information, trauma history and presentation. Optionally, the personal parameters comprise one or more clinical conditions. Optionally, the personal parameters comprise one or more of pediatric trauma history, age, diet, and extent of joint damage.

Optionally, the one or more clinical conditions comprise one or more of osteoarthritis, rheumatoid arthritis, hyperuricemia, and an autoimmune disorder and trauma.

In an embodiment of the invention, the method includes acquiring one or more quantitative measures of at least one joint;

correlating said one or more quantitative measures with a qualitative measure;

storing said one or more quantitative measures in said database; and retrieving said one or more quantitative measure from said database.

Optionally, the one or more quantitative measures is correlated with a qualitative measure using a neural network.

BRIEF DESCRIPTION OF THE DRAWINGS

Exemplary embodiments of the invention are described in the following description, read with reference to the figures attached hereto. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are.

DETAILED DESCRIPTION OF EXEMPLARY EMBODIMENTS

Overview of Osteoarthritis

Figure 1:
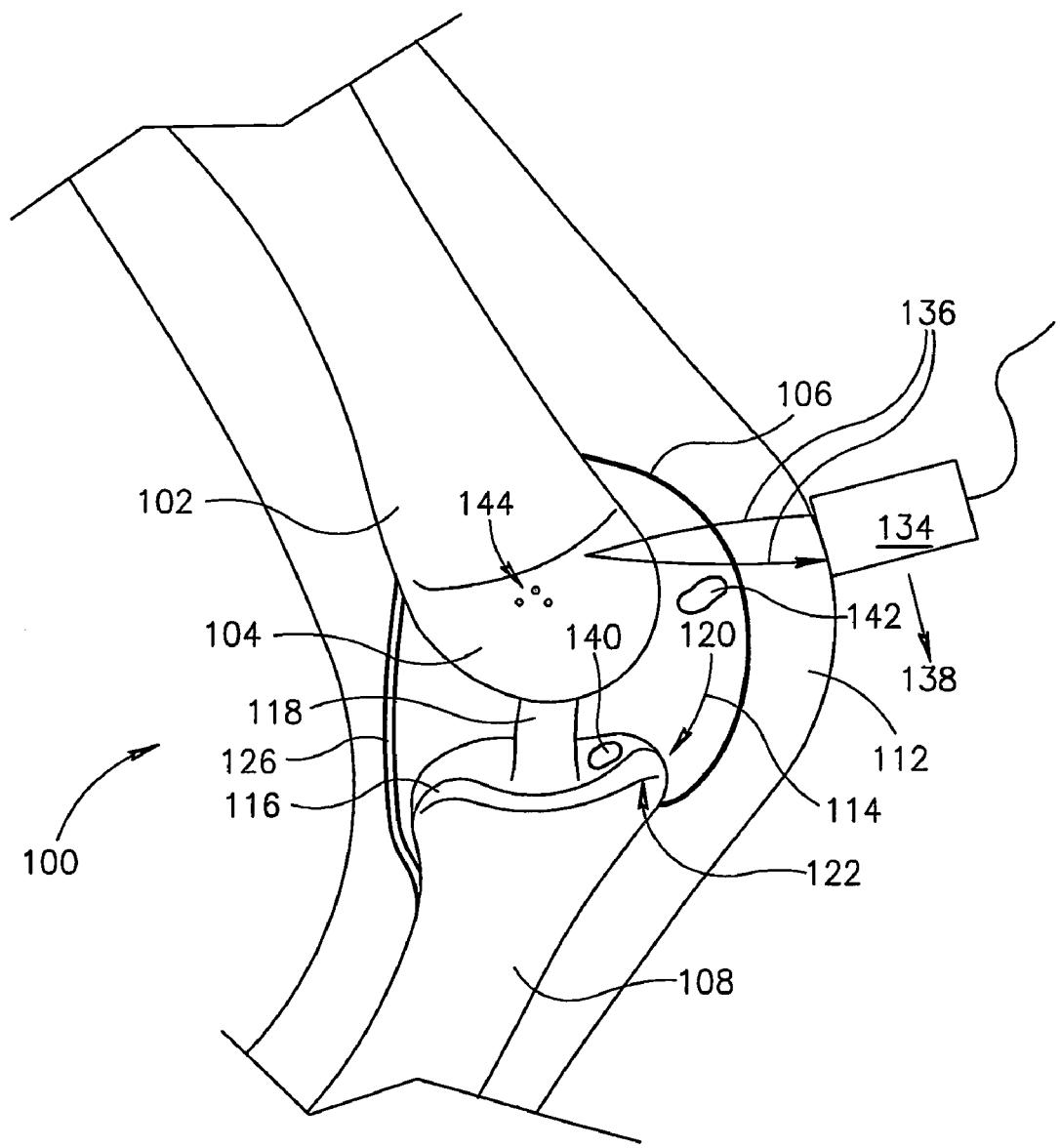
FIG. 1 illustrates quantitative ultrasound measurements of a joint in accordance with an embodiment of the present invention.

FIG. 1 illustrates anatomy for the purpose of making quantitative measurements of joint, for example, to indicate or aid in diagnosis of and/or track osteoarthritis (OA). OA is a major cause of pain in joints such as joint 100. Bones, such as a tibia 108 and a femur 102, in a healthy joint, fit closely together. End of femur 102 is coated with an area of cartilage 104 and end of tibia 108 is coated with an area of cartilage 116 that provide a cushion during motion.

In the early stages of OA, in addition to inflammation and swelling of joint capsule 106, a plurality of focal blisters 144 may form, such as in cartilage surface 104 of femur 106. As OA progresses, thinning occurs in a cartilage surface, such as cartilage surface 116 of tibia 108. An area of eburnation 140 can occur in cartilage surface 116, where cartilage 116 is completely worn away to expose bone 108. Cartilage 116 does not have its own blood supply so damaged cartilage 116 does not heal well and damage to cartilage is often permanent.

With progression of OA, an osteophyte 142 may break off bone 108 and/or cartilage 116 into joint fluid 114. Osteophyte 142 causes further damage to cartilage 116 and joint capsule 106 and makes movement of joint 100 difficult. Untreated, OA progresses until joint 100 becomes permanently painful and stiff to move. On X-ray, late stage OA is characterized by a thin space between bones 108 and 102 of joint 100, signifying overall thinning of the joint cartilage with possible appearance of osteophytes such as osteophyte 142.

As cartilage is not shown clearly on X-ray and often hidden by bone, early stages of OA are often not appreciated on X-ray, let alone graded or quantified. Yet early detection and quantification of OA are important as palliative measures can be taken to prevent progression of the condition and possibly allow early-stage cartilage damage to heal. Treatment of OA often consists of non steroidal anti-inflammatory drugs (NSAID's), taping the joint and bracing the joint to prevent inappropriate movement and relieve pressure during movement. Such therapy is often supplemented with physical therapy modalities such as therapeutic ultrasound and exercises. In equine OA, changes in training regimen are often necessary.

To ease joint inflammation, injections of steroidal anti-inflammatory drugs can be given. In lower extremity imbalance, orthotic shoe inserts, can be helpful. Using ultrasound in diagnosing and tracking OA removes the necessity of repeatedly using imaging with ionizing radiation, so the disease progress can be tracked without risk to the patient and can provide a more precise picture of OA progress.

Introduction to Joint Imaging Quantitative Measurement

An ultrasound measurement of a joint 100 uses a probe 134 that both emits and receives an ultrasound beam 136, which strikes a target tissue such as tissue near a bone 102, and returns to probe 134 with information regarding the tissue.

In an exemplary embodiment of the invention, probe 134 is moved in a direction 138, while touching an area of skin 112, so that it can serially image various joint structures.

In an exemplary embodiment of the invention, probe 134, operates with a frequency of between 5 MHz to 25 MHz. While this range is preferred, probe 134 operates, in some embodiments, with a frequency of 100 kHz or lower to 100 MHz or higher. As an example, a frequency of 8 MHz typically provides a resolution of 0.2 millimeters. A higher frequency such as 15 MHz typically provides a higher resolution, but has less penetration of tissue. In an exemplary embodiment of the invention, probe 134 is used in the imaging method to construct and image or an image is reconstructed from multiple measurements (e.g., for one-, two- or three-dimensional imaging). Alternatively or additionally, a one dimensional or two dimensional phased array or mechanically scanned ultrasound probes may be used to scan a volume.

In an embodiment of the invention, when producing an image of the knee, the patent's knee is bent by approximately 100 degrees (a somewhat smaller bend is illustrated in FIG. 1). The ultrasound probe may be located above the patella. Thus, the cartilage of the femur can be imaged.

An Ultrasound Image

Figure 2:
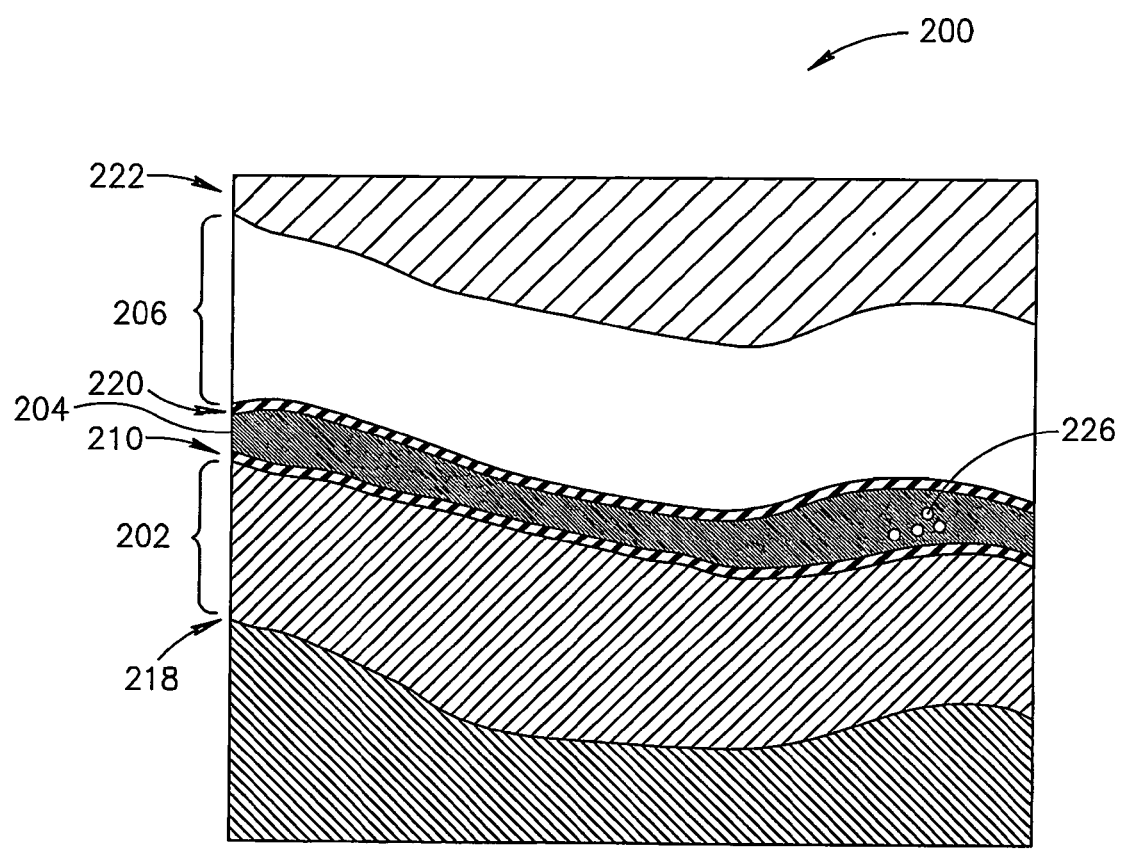
FIG. 2 schematically illustrates a portion of an ultrasound image of a joint for analysis in accordance with an embodiment of the present invention.

FIG. 2 schematically illustrates an ultrasound image 200 of joint structures such as bone 102, cartilage 104 and joint capsule 106 of joint 100, that is produced by probe 134. These structures are, for the purposes of this discussion, healthy structures, with exception of focal blisters 144 in cartilage surface 104 (References are to FIG. 1).

In image 200 of joint 100 structures, a portion of cartilage 204 is shown corresponding to area 104 in FIG. 1 and appears as a dark, curved band 204 with a margin 210 that separates it from a bone portion 202 corresponding to bone area 102 in FIG. 1 and another margin 220 that separates it from a soft tissue portion 206 corresponding to soft tissue area 104 in FIG. 1. In contrast to line 210 that has a width, margin 220 generally has no width, it is just the border between the soft tissue and the cartilage. When the entire portion of cartilage 204 is dark, it is referred to as being "hypoechoic," in that there is less "echo," represented than is represented by a lighter color. In cases where the cartilage is mildly worn, as in this example, there are a few portions of white dots referred to as "speckles" 226 within cartilage 204. This indicates that the cartilage is suboptimal in this portion, caused by, for example, focal cartilage blisters 144 (in FIG. 1) and represent an early stage of OA.

Alternatively or additionally, margin 210 may be less sharp, indicating that the cartilage is worn. When evidence of focal fibrillation is accompanied by a margin 210 that is not sharp, more severe osteoarthritis may be present.

Alternatively or additionally, the linear thickness of a structure is measured. In an exemplary embodiment, cartilage 204 is measured for average thickness by taking the average value of upper cartilage margin 220 and subtracting the average value of lower cartilage margin 210. Thin cartilage is often indicative of more severe osteoarthritic changes.

Cross Sectional Brightness Measurements

Quantitative characterization using measurements of ultrasound image 200 may be obtained in accordance with an embodiment of the invention. using one or more of several quantitative surface or volumetric measurement methods, such as "Cross Sectional Brightness" (CSB). In the cross sectional brightness method, a line is defined manually or automatically or semi-automatically parallel to bone-cartilage margin 210 and the brightness of each pixel along this line is recorded. A single number representing the average brightness of these pixels is calculated.

Taking the average brightness of a line of pixels is repeated for a plurality of lines parallel to line 210 throughout ultrasound image 200. As an example, 30 lines of pixels are acquired from bone portion 202, 15 lines of pixels from cartilage portion 204 and 30 lines of pixels from soft tissue portion 206. In this example, the lines are equally spaced with the number of lines determined by the tissue's thickness on the ultrasound image. Based upon the quantitative measurement requirements, fewer or more lines of pixels can be defined and averaged. For instance, as few as one line can be measured in a single tissue portion, or as many as 100 lines or more can be measured in each tissue portion. Further, the width of each line can vary from one pixel to several pixels (e.g., 30 pixels or more).

The brightness levels are taken from the digital file of the image. They are the values of the color that are given to each pixel. (pixel=picture element). In cases of gray level images the values of the colors usually range between 0=black to 255=white. In cases of colored images Red Green and Blue have values of 0 to 255. Brightness levels can then be defined as the value of one of the Red Green or Blue values or the value of the root of the sum of squares of the RGB values divided by the square root of 3.

Alternatively or additionally, lines of pixels may be taken that are not parallel to margin 210. The position of such lines, for instance, could be based upon joint structure. For instance, a Region Of Interest (ROI) may be defined that encircles a specific portion of a joint. In an exemplary embodiment, a region of interest is planar, and the pixel pattern traces structures that lie on the same planar elevation. Alternatively, pixels may encircle a specific lesion, such as an area of focal cartilage thinning in osteoarthritis, with parallel pixel encirclement lines placed at regularly increasing or decreasing mean radii to provide a 3D surface map of an area Alternatively or additionally, the distance between lines can be less than one pixel in size, for example, using a one-dimensional imaging probe with electronic horizontal scanning having a displacement smaller than the width of a beam. Alternatively or additionally, pixels of different shapes may be used in order to image the joint for specific quantitative measurements, for example, rectangular versus square pixels.

Graphing Quantitative Measurements

Figure 3:
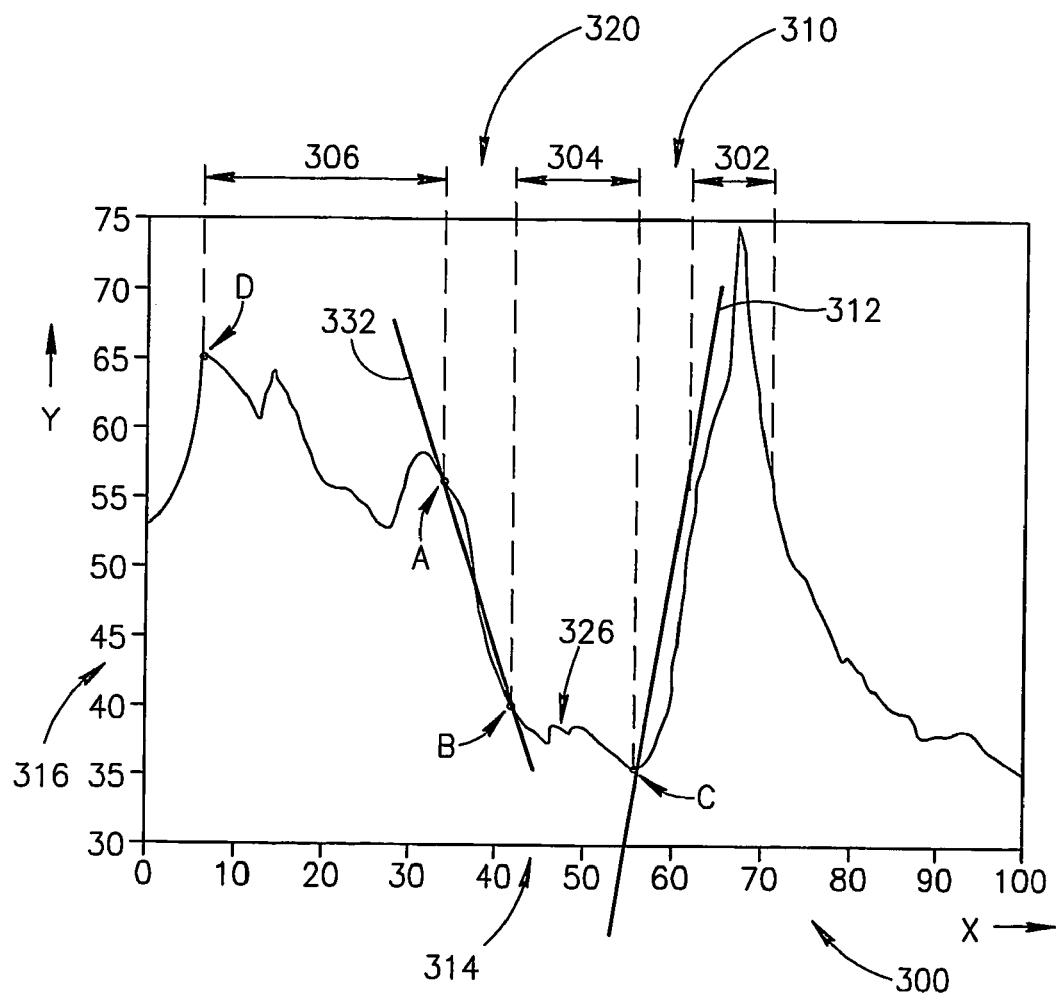
FIG. 3 demonstrates a quantitative graph obtained from ultrasound measurements of a joint.

FIG. 3 is a representative graph 300 of average cross sectional brightness values for the lines measured in ultrasound image 200. An x axis 314 represents the sequential number of each line of averaged pixels. A y axis 316 represents the average value of brightness calculated for each line. A soft tissue portion 306 represents cross sectional brightness measurement of an portion of soft tissue 206. A cartilage portion 304 represents cross sectional brightness measurement of a portion of cartilage 204. A bone portion 302 represents cross sectional brightness measurement of the whitish edge of the bone 210. Graph 300 demonstrates a joint with a cartilage portion 304 that is dark or "hypoechoic" except for an portion of slight elevation 326, corresponding to a lighter portion due to speckles 226 in cartilage 204. This is because the average cross sectional brightness of the lines passing through speckles 226 is brighter than the surrounding cartilage.

In an exemplary embodiment of the invention, graph 300 of Cross Sectional Brightness, is used to ascertain the health of joint structures. Optionally, in cartilage portion 304, a focal brightness 326 is ascertained and correlated with its position within cartilage 102. If focal brightness 326 is a large portion and/or greatly elevated, osteoarthritic damage to cartilage may be present.

A sloped portion 320 occurs between soft tissue portion 306 and cartilage portion 304, defined by a line 332, signifying a rapid transition between cartilage portion 304 and soft tissue portion 306. Such a slope indicates healthy structures such as smooth cartilage at the cartilage-to-soft tissue junction, with adequate thickness of cartilage and soft tissue, and/or intact and non-inflamed soft tissue. A flatter slope and/or a jagged graph in portion 320, can signify that osteoarthritis symptoms are present, such as joint inflammation, damaged soft-tissue-to-cartilage junction and/or cartilage damage. The brightness of the graph of bone margin 302, signifies good structure and a lack of defects such as bone cysts.

In an exemplary embodiment, three parameters, the signal from bone 302, signal from cartilage 304 and slope 332 of soft tissue-cartilage, provide important information to the caregiver about the progression of osteoarthritis.

Alternatively or additionally, the values from portions of graph 300 can be averaged to give a single value for each structure. As an example, the graph line in portion 302 averages out to 67, signifying good bone, the graph line in portion 304 averages out to 39, signifying good cartilage structure health and the slope of graph line 332 is minus 2, signifying good cartilage structure and health. When, for example, average cartilage brightness is increased, slope of graph line 332 is flatter, and average bone margin, portion 302, brightness is decreased, a joint disease, such as osteoarthritis, is indicated.

Additionally or alternatively, in the presence of pathology that requires further examination, another portion of graph 300 is analyzed. For instance, portion between bone 302 and cartilage 304 is smooth and has slope along a line 312. A flatter slope and/or a jagged portion 310, signifies pathology at the bone-to-cartilage interface. When only portion 320 indicates abnormality, it is likely that the pathology is less severe. When both portions 320 and 310 show abnormality the pathology is more severe, such as severe Osteoarthritis.

With the appearance of larger elevation or greater brightness in portion 326, for example, a specific region of interest on image 200 can be computed and analyzed to aid in diagnosis. Such a region of interest can be defined by the physician upon viewing the image or automatically by an image processing software and a control unit that are discussed below. This only defines one coordinate of the damage. The physician may then indicate the ROI manually on the image, based on the coordinate given or an additional image processing algorithm can be used to locate the ROI. For example, automatic determination of coordinate of a region of interest may utilize a template of normal ultrasound values against which the acquired information is compared with variations in values defining a new region of interest. Additionally or alternatively, different measurements can be called for, either by the physician or automatically with alternative data collection methods, such as changing the probe, the type of probe, the number of probes and/or analysis of the collected data.

Alternative Data Analysis Methods

Alternatively or additionally to the cross sectional brightness method, other methods of data analysis may be used to measure a joint and/or suggest or confirm a diagnosis. Two exemplary additional methods for examination of cartilage are Haralick's method and Histogram method.

Haralick's Analysis Method

In an exemplary embodiment of the invention, an analysis of texture is performed using Haralick's image analysis method as is described in Haralick, R. et al., "Textural features of image classification", *IEEE Trans. Syst. Man. Cyber.* Vol 6:610–621, 1973, and Vince, D. G. "Comparison of texture analysis methods for the characterization of coronary plaques in intravascular ultrasound images". This method can be applied to a specific region of interest, for example, delineated on cartilage 204.

With Haralick's method, a co-occurrence matrix is calculated and parameters such as entropy, uniformity, element difference moment of order 1 and 2 and inverse element difference moment of order 1 and 2, can be determined. (Gonzalez R. C. and Richard E. W., "Digital image processing", Addison-Wesley Publishing Company, New York, 1992, and Jain A. K., "Fundamentals of Digital Image Processing", Prentice Hall, Englewood Cliffs, N.J., 1989).

Alternatively or additionally, other measurements, such as the intensity of the cartilage signal, size of spots, arrangements of spots, and/or other texture analysis methods may be used. This is repeated at several locations, perhaps as few as two locations or as many as 100 or 1000 locations. These measurements define the cartilage texture and/or structure that can be correlated with information from a database from which a qualitative assessment can be formulated as described below.

Histogram Analysis Method

In an exemplary embodiment of the present invention measures of gray level Histogram are acquired. In this example, a region of interest is defined manually by the physician or automatically by image processing software. Such a region of interest may, for example, be limited to a partial area of the cartilage, an area that encompasses a specific defect or even a single measurement of entire cartilage surface 116 (or 204 as it is shown in the ultrasound graph illustration). The ultrasound data is computed to find a gray level histogram, which shows the distribution of pixel values and moments of the gray level histogram are computed. (Gonzalez R. C. and Richard E. W., "Digital image processing", Addison-Wesley Publishing Company, New York, 1992) For example one can calculate the first four moments, mean, SD, skewness and kurtosis. Other statistical parameters such as 3rd quantile or inter quantile range of the gray level histogram can also be calculated. These measures can be used for grading. In general, they are believed to correlate with the "golden standards" used in the field.

Grading Cartilage Using A Combination of Parameters

A combination of parameters, such as from those noted above, may provide more insightful quantitative data on the state of cartilage. Alternatively or additionally, specific combinations can be deduced from statistical methods that compare the parameters obtained using the ultrasound image and a grading parameter obtained by a "golden standard" such as MRI (H. K Gahunia, P. Babyn, C. Lemaire, M. J. Kessler, K. P. H. Pritzker, "Osteoarthritis staging: comparison between magnetic resonance imaging, gross pathology and histopathology in the rhesus macaque", *Osteoarthritis and Cartilage*, vol. 3, 169–180, 1995.)

For example the following exemplary equation results in a grading of the cartilage quality through comparison to other grading measures.

$$\text{Grading} = -1.6 + 1.0 * CST + 0.2 * CB - 0.054 * BB \quad [\text{Eq. 1}]$$

where CST (cartilage soft tissue) is the slope of the cartilage-soft tissue margin, CB (cartilage brightness) is the minimum cartilage brightness and BB (bone brightness) is the maximum bone brightness as they appear in cross sectional brightness graph 300. This grading is based on a grading of a physician from ultrasound images. Other bases can, of course, also be used to generate grading formulas.

It should be understood that the above measurements (as well as some of the other quantitative measurements described in this application) are somewhat dependent on the ultrasound device used as well as on the settings of the device and, to some extent, on the overlying structures in the particular patient. Furthermore, calibration of the image brightness values should be performed prior to the cross sectional brightness calculation. This calibration can be performed by obtaining an image of a known phantom. The value of the brightness of a part of the phantom is then divided to an originally obtained brightness of the same part. The results gives a value by which all of the new images brightness values should be divided. For reference, the above and following values are based on measurements made with a "synergy B" scanner of GE_Diasonics, utilizing a linear array probe (11/MI/33/LA). The probe operates at 12 MHz and has an array dimension of 50×5 mm. A B scan having the following characteristics was used: depth of image 40 mm, gain 55, dynamic range A, post processing 2, power 100, sharp 0, frame average High, reject 0.

In an exemplary embodiment, two points, C and D, are used to determine points A and B which determine the slope of line 332.

The dimension of the slope is in brightness levels/(number of pixels), which is approximately equal to brightness/mm. Due to variations in taking the images, calibration, etc., the brightness values and slopes can be expected to be correct to within a few percent. Point C is determined by tang the minimum brightness of cartilage portion 304 of graph 300, and in this example, corresponds to a value of 37 along the Y-axis. Point B is determined by the first point following point C that has a brightness of 110% of value C.

Point D is the Maximum brightness of soft tissue portion 306, in this example, it has a value of 65 on the Y axis. Point A is determined by taking the first point with a brightness value of 90% of point D and has a value of 33 on the X-axis in this example. When using other parameters to calculate such parameters as the CST, the formula is changed to reflect these parameters.

The grading obtained from Eq. 1 results in a number usually between 0 to 6 where values close to 0 indicate that the cartilage is healthy and values close to 6 indicate that the cartilage is unhealthy. A value of 6 on the ultrasound scale, for instance, corresponds to a value of "4" in the MRI parameters This grading allows the compilation of multiple measurements into a single quantitative value so that condition of a joint graded in this fashion can be easily ascertained by a caregiver.

Alternatively or additionally gradings obtained by X-ray (Kellgren), CT or clinical indices (WOMAC) can serve as the golden standards to which the parameters obtained using the ultrasound image should be correlated to.

Further Quantitative Measurement of Cartilage

Figure 4:
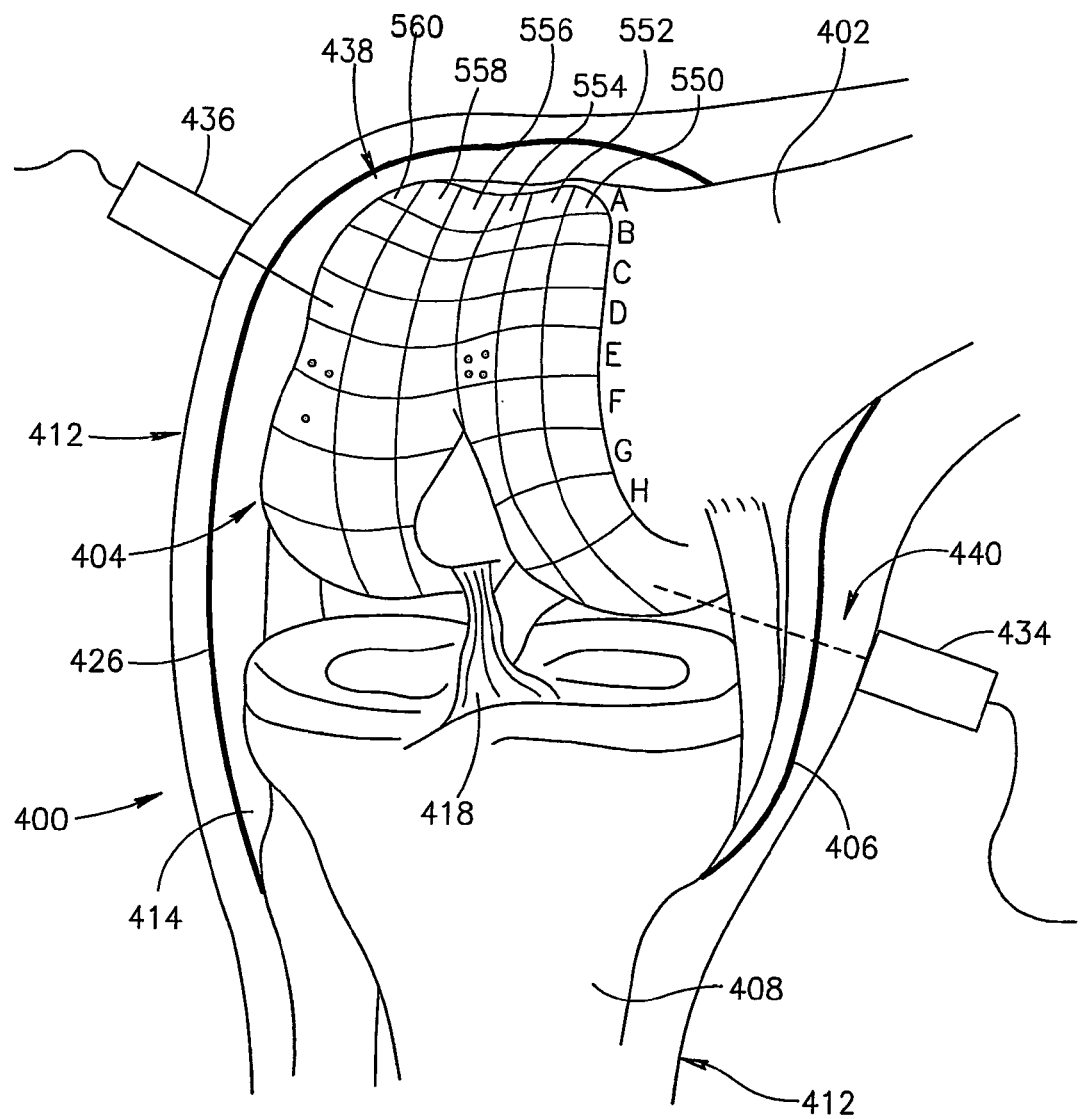
FIG. 4 illustrates quantitative measurement of cartilage in accordance with an embodiment of the invention.

FIG. 4, illustrates gathering quantitative measurements on a joint 400 using a single probe 436 that both transmits and receives data. Alternatively or additionally, two probes, 436 and 434 can be used in an alternative method described below. The quantitative measurements of joint 400 are specific for evaluating or indicating specific disease states as will be explained further on.

In examination of cartilage 404, bones, 402 and 408 are flexed at approximately 100 degrees to give a relatively unobstructed examination of cartilage 404. The obtained ultrasound images are processed to give the measures mentioned above. Alternatively or additionally, a knee joint 100 can be placed in the fully extended position. Such a position allows a smaller portion of cartilage 404 to be examined, but a joint capsule 412, that surrounds joint, 404, is in a relaxed position and joint fluid 414 within joint capsule 412, can be better visualized by probe 436.

Alternatively or additionally, joint 400 can be placed in a variety of degrees of extension to view other joint structures as will be demonstrated below. Alternatively or additionally, joint 400 can be viewed during motion, on or off weight bearing, or during performance of specific types of activity, as will be described below.

In an exemplary method, ultrasound probes 436 and 434 are attached to a gantry that moves at a fixed rate in relation to the joint surface. This generates an image or values that can be fixed in position either relative to the cartilage boundaries or relative to each other. By way of example, cartilage 404 is divided into a grid 438. Grid 438 has been divided into transverse sectors 550, 552, 554, 556, 558 and 560 and longitudinal sectors A–H. These are one centimeter in square area.

In an exemplary embodiment of the present invention cartilage 404 is evaluated for pits. By way of example, such evaluation is accomplished using the CSB method described above. Based on this, specific sectors are targeted for further study. In an exemplary embodiment, data is compiled from sectors that have pits. For example, such data is compiled from a sector 554E, which has 4 pits, a sector 560E that has 2 pits, and a sector 560F that has one pit.

Cartilage Thickness Measurement

In an exemplary embodiment of the present invention, average cartilage thickness (CT) in sectors with pits is measured. By way of example, sector 554E has a CT of 1.2 millimeters, sector 560E has a CT of 1.3 millimeters and section 560F has a CT of 1.4 millimeters. Cartilage from a sector without pitting, such as a sector 554D is measured for CT and used as a basis of comparison. Sector 554E for example has a CT of 2.2 millimeters.

Additionally or alternatively, quantitative measurements taken with various methods are correlated for each defined ROI portion. For example the CSB method can be correlated with the histogram statistic method and conveys information on several aspects of joint structure quality in a value.

Square Area Cartilage Defect Measurement

In an exemplary embodiment of the present invention, other measurements are acquired from the cartilage, such as the square area of pits (PA) per sector. By way of example, sector 554E has a PA of 0.85 square millimeters, 560E has a PA of 1.1 square millimeters and 560F has a PA of 1.35 square millimeters.

Average Depth Cartilage Defect Measurement

In an exemplary embodiment of the present invention, the Average Cartilage Pit depth (CPD) is measured. Sector 554E has a CPD of 0.6 millimeters, sector 560E has a CPD of 0.6 millimeters and sector 560F has a CPD of 1.3 millimeters. By utilizing different collection methods, the accuracy of the measurements can be increased. For instance, by using invasive probes, such as needles with a small diameter, or by increasing the frequency, the accuracy can be increased.

Figures 5A, 5B, 5C:
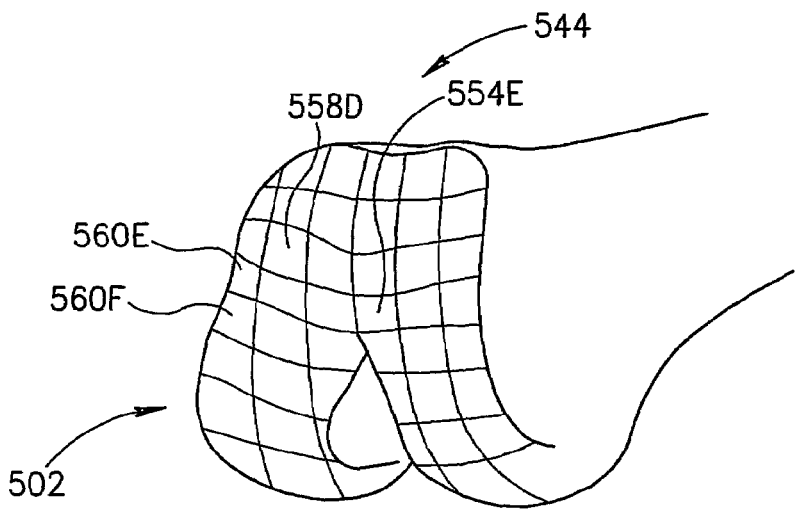
FIG. 5A is an illustration of a joint reference grid for quantitative measurements in accordance with an embodiment of the invention.
FIG. 5B is an illustration of a table of quantitative measurements in accordance with an embodiment of the invention.
FIG. 5C is an illustration of a key for reference of values in accordance with an embodiment of the invention.

In an exemplary embodiment of the present invention, this information is compiled into a database chart including FIG. 5A that is a reference grid 502 and FIG. 5B that is a table 530 of quantitative measurements. A key 532, FIG. 5C, shows reference values of table 530.

By way of example, table 530 is shown with the data from sector 554E, sector 558D sector 560E and 560F. Data from FIG. 4 is used to compute further quantitative ultrasound joint measurements as described below.

Cubic Volume Cartilage Defect Measurement

In an exemplary embodiment of the present invention, the square area of pits (PA) in each sector and the Average Cartilage Pit Depth (CPD) are used to give the Cubic Volume of Pitting (CPV) in each sector. By way of example, Cubic Volume of Pits (CPV) in row 560 is 0.560 cubic millimeters. CPV of row 222 is zero as this sector contains no pits. CPV of row 524 is 0.682 cubic millimeters and CPV of row 526 is 0.65 cubic millimeters.

Quantitative Value for Cartilage Volume Measurement

Total Cubic Cartilage volume (TCV) comprises the cartilage area, which in this example is 100 millimeters, multiplied by the Cartilage Thickness (CT) in millimeters.

In an exemplary embodiment of the present invention, the CPV is subtracted from the TCV to give the Cartilage Cubic Volume (CCV) 534. This is an example of a quantitative measurement that summarizes a number of values for a given sector of the cartilage surface 404.

Significant Quantitative Cartilage Values

Alternatively or additionally, the data is expressed as an array of two or more numbers, such as CCV and P (the number of pits) (CCV, P), to give information about the cartilage volume and number of pits in a given sector. For example (CCV, P) for sector 554E is (121.48 , 4), for sector 558D (CCV, P) is (442, 0), (CCV, P) for sector 560E is (135.58, 2) and for sector 560F (CCV, P) is (138.35, 1). By way of example, cartilage donor sites require a CCV above 140 cubic millimeters and a P of 0 to 1.

Alternatively or additionally, the data is collected from all sectors and expressed as an average value of sectors. In an exemplary embodiment, the average CCV of all pitted sectors is 131.87 cubic millimeters while the average number of pits is 1.75, giving (CCV , P) AV. of (131.87, 1.75) in pitted sectors 304E, 560E and 560F.

By way of example, such information provides a basis for further examination of particular sectors. In an exemplary embodiment of the present invention, sectors with low CCV 534 are targeted for measurement of adjacent cartilage surfaces. Adjacent cartilage surfaces are measured to determine the extent of a particular condition. By way of example, in traumatic damage to joint cartilage, sectors adjacent to a sector with extensive damage are examined to determine the extent, shape and depth of the resultant damage.

Quantitative Measurement for Cartilage Grafting

In an exemplary embodiment of the present invention, information about the extent of traumatic damage and/or arthritic damage to joint cartilage provide a picture that guides a surgeon in cartilage grafting during joint reconstruction.

By way of example, the three areas with pitting 554E, 560E and 560F indicate a possible need for cartilage replacement. Sector 558C and other sectors with similar measurements of thicker cartilage without pits, indicate that such sectors are suitable as cartilage donor sites.

Other Joint Structure Quantitative Measurement

When cyst extent is measured in such disease states as hyperuricemia, smaller areas, such as five millimeters square, can be assessed using broadband ultrasound attenuation, for example, with lower attenuation of the signal indicating a possible cyst.

In an exemplary embodiment of the present invention, additional joint aspects are measured and quantified. By way of example, density or resilience of joint capsule, ligaments, tendons and other soft tissue structures that make up the joint are measured.

Database Analysis of Quantitative Measurement

In an exemplary embodiment two or more quantitative ultrasound joint measurements are compiled into a database according to personal parameters such as age, sex or ethnic group, athletic or exercise regimen, or systemic parameters such as genetic or traumatic joint disease states. Additionally or alternatively, two or more quantitative ultrasound are compiled into a database on the basis of a qualitative association with measurements from, for example, X-ray, MRI, or isotope uptake. Additionally or alternatively, two or more quantitative measurements are combined with each other to provide a qualitative parameter of joint state and entered into a database.

In an exemplary embodiment, a database containing quantitative and qualitative joint information that are correlated with a variety of personal, systemic and qualitative parameters is used to provide a qualitative characterization of one or more joint measures acquired from a subject. In an exemplary embodiment, such analysis of information is provided on a visual display or in a printed readout of information where, for example, the data is organized into three dimensional model of said joint.

Correlative Database Update

A method for continued database update and enhancement from acquired data is provided so that the database is continually expanding the scope of correlative information to which newly acquired data is compared. Such update and enhancement provides for establishing a correlation between acquired quantitative measures and quantitative, qualitative measures that are organized and correlated according to a variety of quantitative and qualitative measures and personal parameters. In an exemplary embodiment, the establishment of a correlation of database information with acquired quantitative measures utilizes associative formulae that are contained in processing software of the database. Additionally or alternatively, input of acquired information is accomplished through a neural network whereby a new correlation of parameters and quantitative measures are established to provide new values, qualitative correlation, or measurement standards to be used for analyzing further values that are acquired. Such new values are then, for example, used in the analysis of all further quantitative measures in the database.

Quantitative Measurement Database of Athletic Activity

In an exemplary embodiment of the present invention the database is organized based on individuals with common activity interests. And example of common activity interest is groups of swimmers, skiers or marathon runners. In an exemplary embodiment of the present invention the data is organized according to intensity of common activity and such factors as health status and diet.

In an exemplary embodiment of the present invention, the database of quantitative ultrasound joint information correlates joint measurements from athletes with any of a number of joint characteristics such as cartilage, capsule thickness, and other aspects of the knee joint.

Joint Position and Quantitative Measurement

Joint pathology may only present as a symptom in a certain position, such as pain of the elbow when the hand is maximally rotated on the arm or at a specific point during range of motion. By measuring motion and contact area, a number of quantitative measurements can be derived. In an exemplary embodiment, the ultrasound database includes data that is acquired from measurements of joint structures with the joints in a variety of positions such as flexion, extension, supination, eversion, on weight bearing, off weight bearing.

In an exemplary embodiment of the present invention, quantitative ultrasound joint measurements are acquired during and/or following regimens such as walking, running and/or aerobic exercise. Such database information, for instance, provides guidance to training athletes. By comparing joint movement of a single athlete to that database, potentially damaging joint positions are averted or splinted, preventing joint damage during athletic competition.

Quantitative Measurement and Treatment Regimen

An embodiment of the present invention correlates the ultrasound database with pathologic conditions such as joint pain, inflammation, imbalance and trauma.

By way of example, the database includes quantitative data on treatment regimen in joint inflammation, healing time, and/or treatment sequella of athletes. The database correlates a treatment regimen such as local or systemic medication, orthotic braces and/or physical therapy to a specific athletic activity.

Additionally or alternatively, the database correlates quantitative ultrasound measurements in genetic joint diseases with disease-related blood titers. The correlative database is used in predicting disease course and/or giving treatment to diseases such as rheumatoid and psoriatic arthritis. Additionally or alternatively quantitative ultrasound joint measurements are used in detection and treatment of joint changes in genetic-related based joint diseases.

Global Quantitative Measurement

In an exemplary embodiment of the present invention, a global ultrasound measurement, such as CCV, is made of an entire joint to assess treatment in cases of worn or damaged cartilage. Such measurement directs the caregiver in cartilage replacement, such as whether to replace a single condyle, or the entire knee.

Through Probe for Collection of Data

FIG. 4 illustrates a "through" method of collection of data in which an ultrasound probe 434 is an emitter of ultrasound waves and a probe 436 is a receiver of ultrasound waves with ultrasound waves traveling in a line 440 through a joint 400. Probes 434 and 436 are used to measure an area of cartilage 404 of a knee joint 400 or other structures. Optionally, the two probes are coupled to each other, for example, using a gantry (not shown) to fix their relative positions and/or orientations.

In the through method, typically, the frequency emission is in the range of 200 kHz to 10 MHz. The through method frequency range differs from that of the Echo/Imaging method where the range can be, typically, 5 MHz to 25 MHz because the Echo/Imaging method is used to determine spatial structure, requiring more precise resolution. The through method does not necessarily image the joint structure and uses a lower frequency to acquire data from greater tissue depth with higher signal to noise. However, higher or lower frequencies may be used in either method.

In one embodiment of the through method, when the structure measured is covered by a thick layer of soft tissue, a frequency closer to 200 kHz is used, as a higher frequency attenuates while going through several centimeters of tissue. Alternatively, when the structure being measured is more superficial, and greater clarity of microstructure is desired, a higher ultrasound frequency, such as 10 MHz or even 50 MHz or higher, may be used. The use of far higher frequencies with greater penetration, or lower frequencies with greater tissue clarity, may be facilitated by suitable probe design.

In using this method in a knee joint 412, probes 436 and 434 are held on the sides of the knee when the leg is fully extended. Alternatively, as shown, probes 436 and 434 are held at either side of the joint anterior or at the sub patella notches, while the knee is flexed at 90 degrees. The data is analyzed based on spectral analysis (frequency domain) and/or temporal analysis (time domain) of the received ultrasound signal, to characterize a biologic tissue.

Osteophytes, for example, filter out high frequencies. When comparing the spectrum of a signal obtained from a healthy joint and an osteoarthritic joint, the healthy joint spectrum includes higher frequencies. Changes in signal frequency characteristics may establish the existence, size and/or quantity of osteophytes.

Echo Method for Collection of Data

The Echo method, shown in FIG. 1, uses a single probe such as traducer 436 operating in a pulse echo mode, where the same probe both emits a signal and receives the pulse echo. Typically the probe emits ultrasound in the range of 5 MHz to 25 MHz. Probe 436 is connected to a controlling device consisting of a pulse receiver and signal recorder.

The analysis is based upon time domain and/or frequency domain analysis of the ultrasound signal. For instance, the cartilage entry and exit echoes are identified and the signal received between the two is analyzed to ascertain the quality of the cartilage in terms of homogeneity versus graininess. Alternatively, a single probe is moved along the cartilage for joint scanning purposes to map the entire joint without producing an image.

Analysis of Alternative Joint Structure

Figure 6:
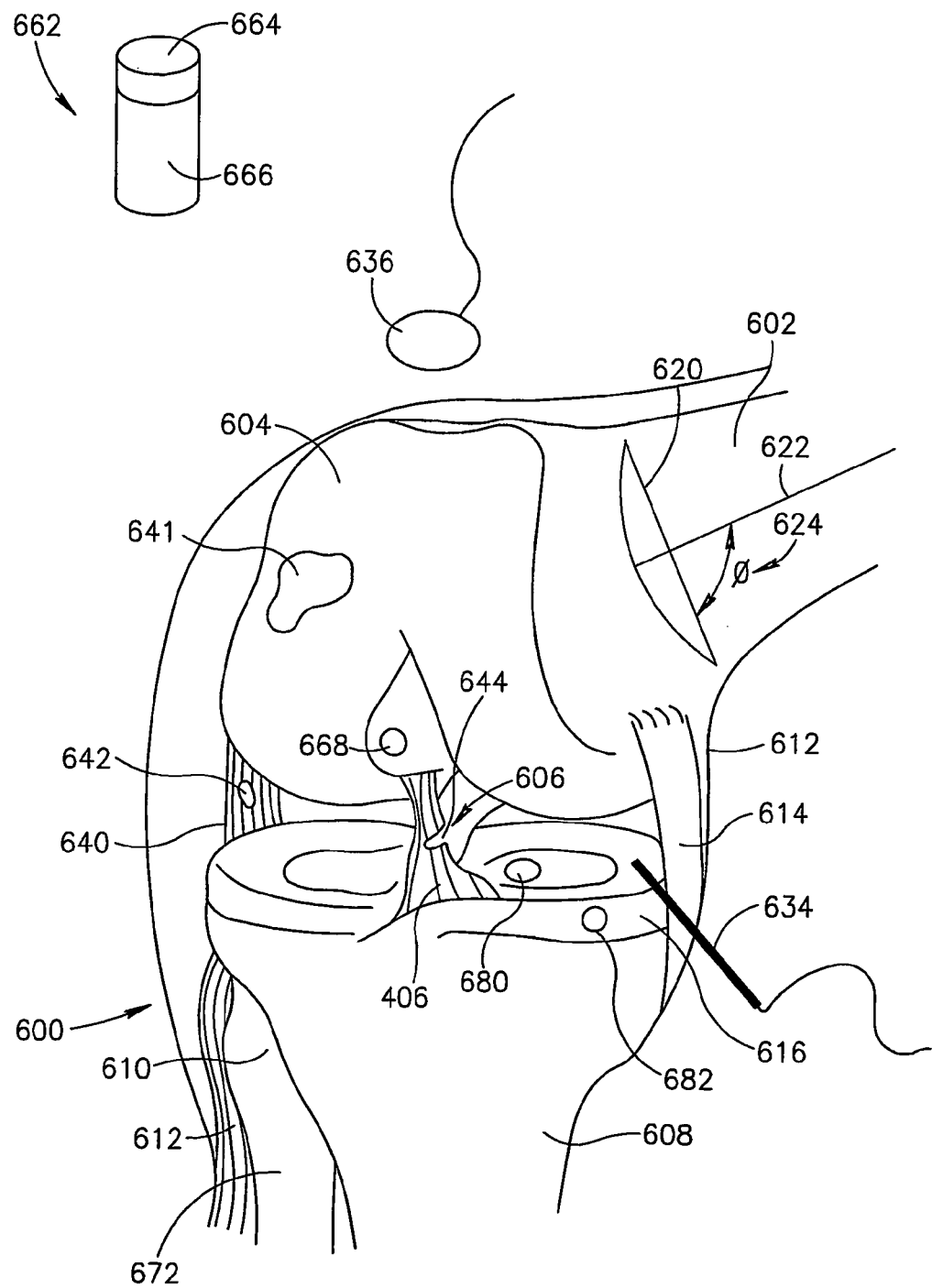
FIG. 6 illustrates anatomy for describing quantitative ultrasound measurement of a plurality of different joint structures in accordance with an embodiment of the invention.

In an exemplary embodiment, FIG. 6 illustrates quantitative ultrasound measurement of a plurality of different joint structures with a probe 636. Backscatter of ultrasound signal can be used to measure the presence of an inclusion body 642 in collateral ligament 640 and aids in location and removal of an inclusion body 642 during surgery. Backscatter of ultrasound signal is described in: Wear, K A, Garra, B S, "Assessment of bone density using ultrasonic backscatter", *Ultrasound Med Biol* 1998 June; 24(5):689–95.

Alternative Joint-Type Quantitative Measurements

Alternatively or additionally probe 636 measures joints that do not contain joint fluid. An example is a joint 600 between fibula 672 and tibia 608, that is referred to as a syndesmosis. This joint displaces in high fractures of fibula 636. By way of example, probe 636 measures disruption between fibula 672 and tibia 608 in a damaged joint by measuring the amount of attenuation of the signal. When the syndesmosis is disrupted, there is less attenuation of signal and a lower frequency absorption. Alternatively, probe 636 can measure other parameters in this joint or in other syndesmotic joints. For instance, by measuring backscatter, the present and/or amount of bone fragments can be assessed. An increase in bone fragments, for example, can cause increased backscatter of acoustic signal, as described in: Wear K A, Garra B S, "Assessment of bone density using ultrasonic backscatter", *Ultrasound Med Biol* 1998 June; 24(5):689–95.

In an exemplary embodiment of the present invention, ultrasound probe 636 measures a cyst 682 in a joint structure. By way of example, cyst 682 contains material such as metal debris that has broken off implanted bone hardware or a tumor such as in a Giant Cell tumor and quantitative ultrasound measurement, for example, can made with Broadband Ultrasound Attenuation or Dispersion of ultrasound signal.

Quantitative Measurements and Blood Data

In an exemplary embodiment of the present invention, the level of Uric Acid in the blood and/or the period of elevation, are correlated with quantitative measurements of uric acid cysts in joint structures.

Cartilage Grafting and Quantitative Measurements

An exemplary application of the present invention is, as noted, in placing cartilage implants. A cartilage plug 662 shown contains a cartilage surface, 664 and a bone portion 666. Typically, cartilage plug 662 is cylindrical in structure and acquired from a donor area 668 of joint 600 where the cartilage generally does not bear weight and hence contains fewer pits in its surface. As an example, a recipient area bore 680 is made in cartilage 616 to the same depth as the height of cartilage plug 662 and cartilage plug 662 is placed into recipient bore 680

In an exemplary embodiment, a needle shaped ultrasound probe 634 contains an ultrasound transmitter and ultrasound receiver, or a small array of transducers and is used for intra-operative joint inspection. Additionally or alternatively, an ultrasound probe can provide a phased array or swept beam ultrasound.

Growth Plates and Quantitative Measurements

Figure 7:
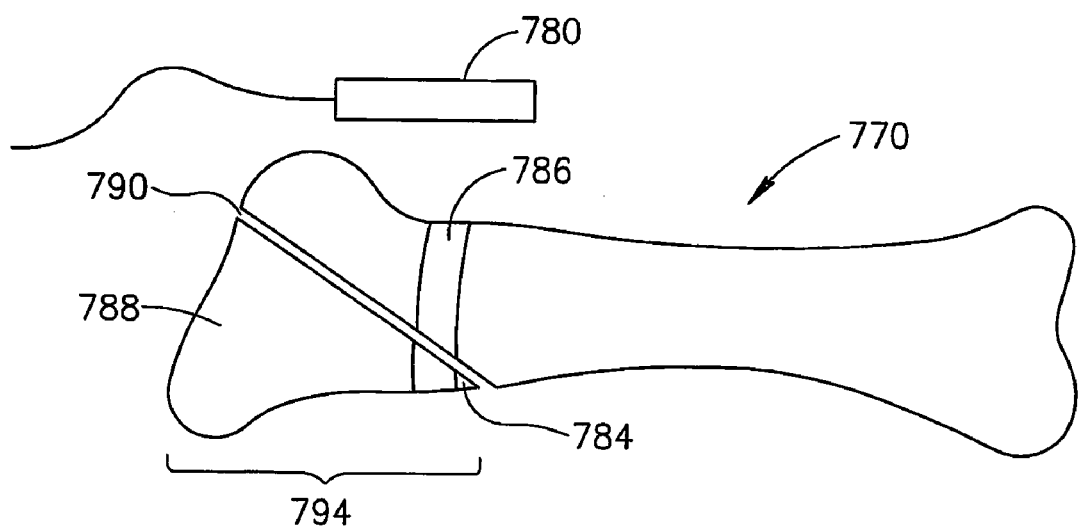
FIG. 7 illustrates anatomy for describing ultrasound measurements of a damaged pediatric joint in accordance with an embodiment of the invention.

FIG. 7 shows an ultrasound probe 780 making quantitative measurements of a damaged pediatric bone 770. In an embodiment of the present invention this information is correlated with a database specific to a subgroup such as growing joints in children.

Pediatric bone 770 is typical for bones such as the humorus and radius that make up the elbow joint. Pediatric bone 770 contains a metaphysis 784, a growth plate 786 and an epiphysis 788. For instance, the speed of sound in cartilage through growth plate 786 is about 1700 meters per second (m/s) while speed of sound in bone, such as through metaphysis 784 is about 2000–4500 m/s, depending on probe localization and age.

In an exemplary embodiment of the present invention pediatric measures, such as quality, width and/or volume of growth plate 786, are compiled into a database. Abnormal values may indicate a need, for example, for blood testing of growth hormone levels with the need for such tests being signaled, for example, by data processing software, as will be explained below.

Pediatric bone 770 has a fracture 790 that extends through epiphysis 788, growth plate 786 and metaphysis 784 with a fracture fragment 794 that is displaced on bone 770.

The broadband ultrasound attenuation from area 794 is increased due to the presence of ossified bone 794 that has separated from bone 770. Additionally or alternatively, by taking measurements radially around bone area 794, fracture 790 is located and its extent is determined. For example, acoustic speed of sound will show marked changes as the signal passes normal to area 790 and through fracture 790 while the speed of sound of signal passing parallel to area 790 will appear almost normal. Additionally or alternatively, Dispersion of acoustic signal from any angle to fracture 790 in area 794, will change relative to that of a non-fractured area bone.

In an exemplary embodiment of the present invention, quantitative ultrasound measurements provide information on diagnosis, prognosis, and preferred therapy in treatment of injury of metaphysis 784, growth plate 786 and epiphysis 788. For example, measurements of displaced fragment 794 that are correlated with the database provide information as to the necessity for open surgical reduction of fragment 794 as opposed to closed manipulation so that fragment 794 heals in the proper position. Post reduction quantitative ultrasound measurements demonstrate the progress of proper incorporation of fragment 794 into the joint structures.

Equine Quantitative Measurements

Figures 8A, 8B:
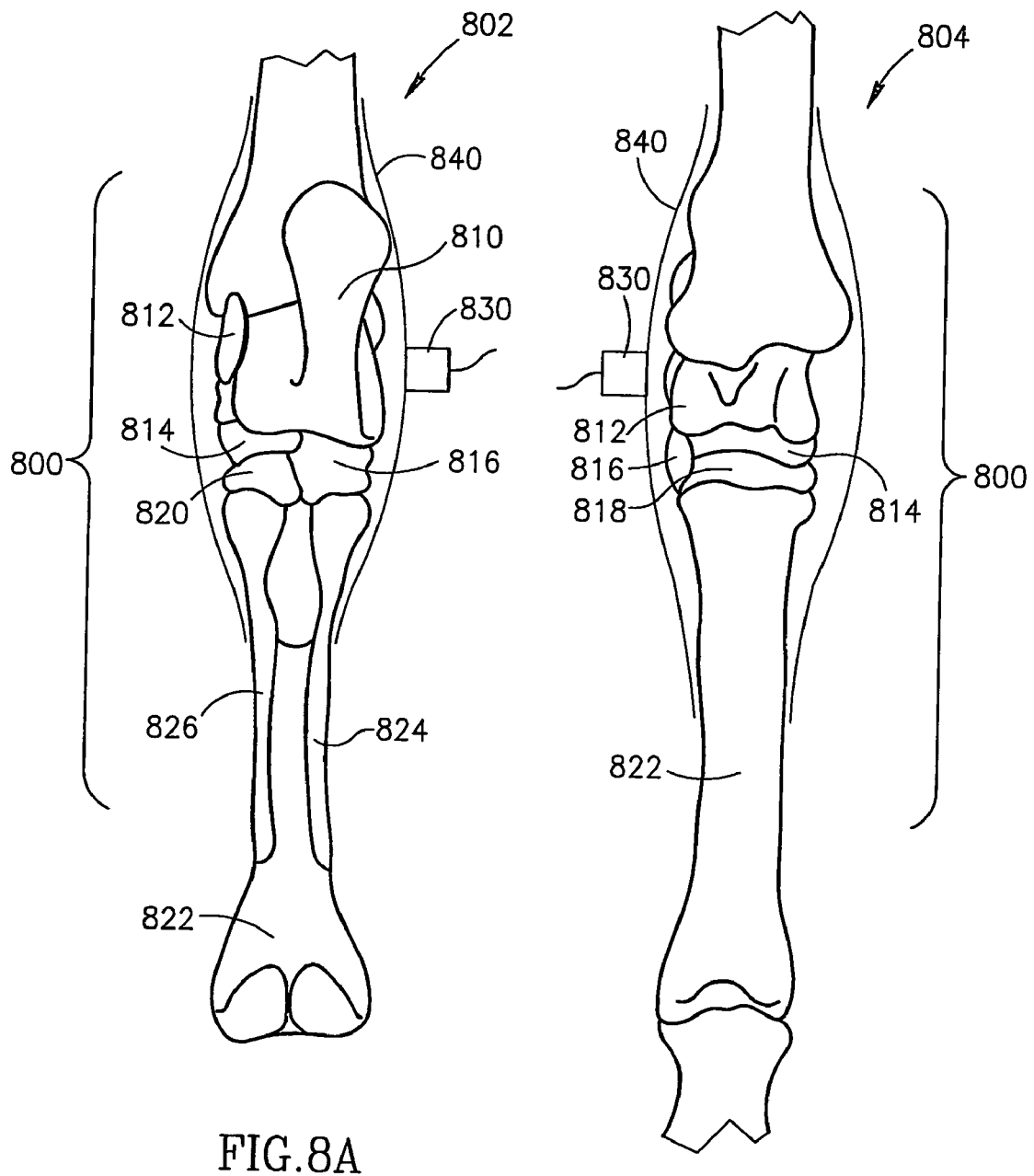
FIG. 8A illustrates anatomy for describing ultrasound measurements of an equine talocrural joint, shown in a caudal view, in accordance with an embodiment of the invention.
FIG. 8B illustrates anatomy for describing ultrasound measurements of an equine talocrural joint, shown in a cranial view, in accordance with an embodiment of the invention.

FIGS. 8A and 8B illustrate two views of a talocrural joint 800 of a horse, with 802 being a Caudal view and 804 being a Cranial view. The equine talocrural joint 800 is made up of a Calcaneus 810, a Talus 812, a central tarsus 814, a fourth tarsal 816, a third tarsal 818, a first and second tarsal bone 820 that is fused, a third metatarsal 822, a fourth metatarsal 824 and a second metatarsal 826.

A probe 830 is positioned directly against the soft tissue 840 over Talus 812 of the equine talocrural joint 800 as seen in Caudal view 802 and in Cranial view 804, giving information about equine talocrural joint 800. The equine talocrural joint is highly susceptible to inflammation due to overuse and imbalance. Joint inflammation is characterized by changes in the viscosity of joint fluid, presence of inflammatory cells in the joint fluid and thickening of the joint capsule, among other symptoms. With increased effusion, the speed of sound decreases.

In an exemplary embodiment of the present invention, equine talocrucal joints are examined for OA and a database is compiled. By way of example, information obtained and analyzed from such a database allows rapid diagnosis of joint inflammation and osteoarthritis and is used to predict, for example, the ability for a racehorse to recover from a given injury, or injury cycle.

A Quantitative Measurement and Analysis Apparatus

Figure 9:
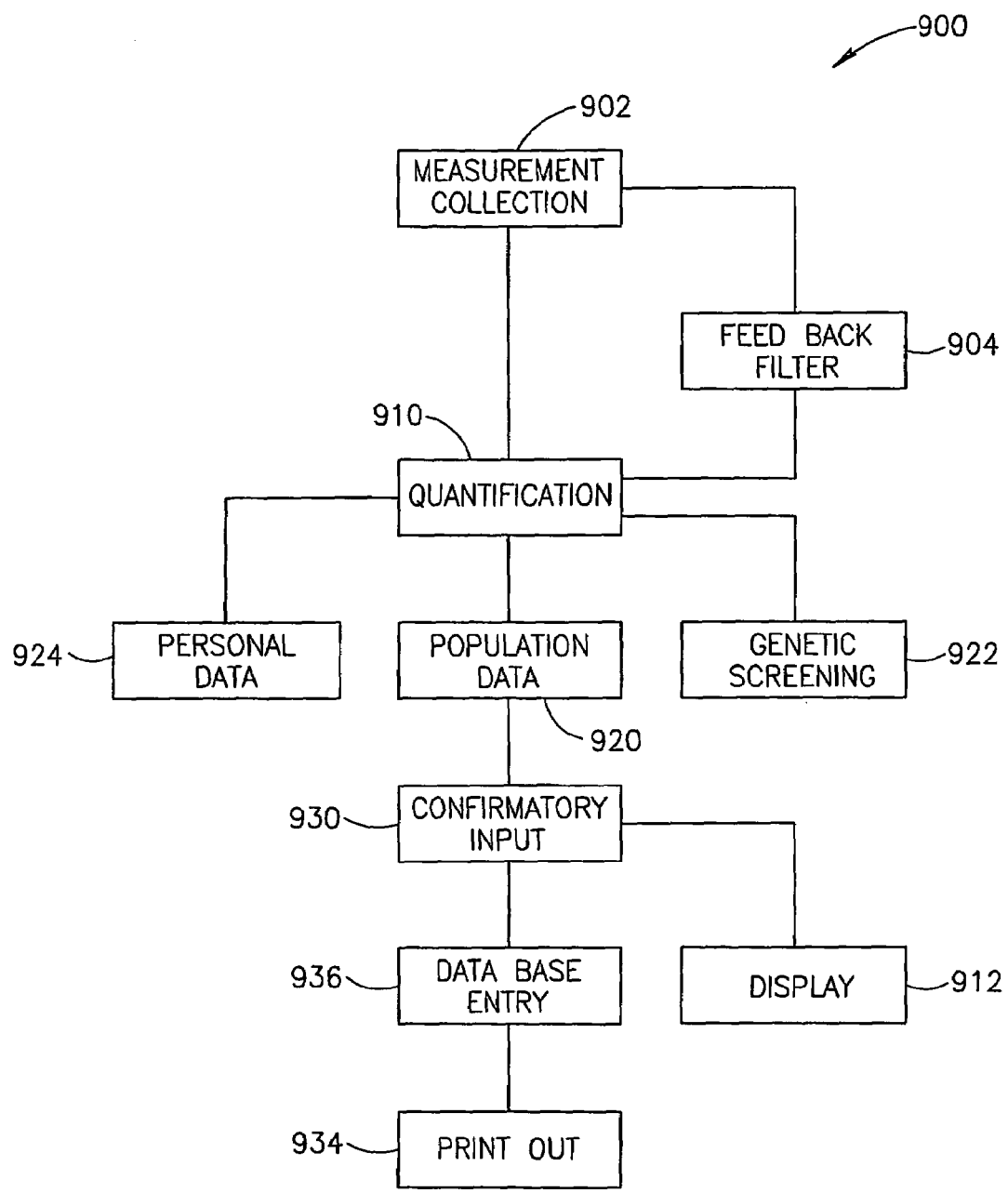
FIG. 9 is a block diagram of a computational system used in quantification of joint structure measurements in accordance with an embodiment of the invention.

FIG. 9 is a block diagram 900 showing an embodiment of a computational system used in quantitative joint structure measurements.

In an exemplary embodiment of the present invention, data is collected in an ultrasound measurement collector 902. By way of example, ultrasound probes 434 and 436 make measurements of pitting in an area of cartilage as part of measurement collector 902.

In an exemplary embodiment of the present invention, a feedback filter 904 processes the information. Feedback filter 904 data is processed to determine the quality of the ultrasound signal and adjusts changes in such ultrasound parameters such as signal amplitude Alternatively or additionally, feedback filter 904 requests an alternative ultrasound collection technique that is appropriate for generating specific joint data. As an example, feedback filter 902 may request region of interest imaging data with the echo transducer method after receiving speed of sound data compiled with a through traducer method, providing necessary additional information.

In an exemplary embodiment of the present invention, measurements are sent to a quantification system 910 that suggests additional quantitative ultrasound measurements based upon the evolving picture of the data in comparison to database quantitative measurements.

In an exemplary optional embodiment of the present invention quantitative data is processed in a population comparison system 920 where information is analyzed according to population data such as the subject's age, weight, and/or ethnic character. Alternatively or additionally, data is analyzed by the database according to the type and amount of sports activities the subject is engaged in.

Optionally data 910 is processed by a genetic screening system 922 genetic tendencies to develop a joint disease such as Rheumatoid Arthritis are determined. Optionally data 910 is sent to a personal data system 924 where the data is compared to prior measurements acquired on the same subject such as prior measurements of cartilage pitting.

A confirmatory input system 930 correlates the data, according to a software processing program, comparing it to existing data. System 930 also may analyze the data to determine further measurements that need to be acquired such as data input from a new region of interest. Optionally, confirmatory input system 930 suggests one or more blood tests that need to be performed such as the need for blood uric acid testing in the presence of uric acid cysts in the joint.

In an exemplary embodiment of the present invention, the information from all additional testing is entered into confirmatory input 930 where it is processed and sent to a database entry system 936 where the data is entered order to augment an existing database.

Confirmatory input 930 generates a display 912. Typically, the display displays inter alia an image similar to wire frame 544, a table 530 and/or a key 532 combining information about the joint, population comparison and/or disease state noted above. Alternatively or additionally, the data is placed within a grid 544, with the data of each sector being displayed in numbers contained within the sector. Optionally, each sector contains a large amount of data that can be viewed when the operator chooses a particular sector. As an example, grid 544 is shown on a touch-sensitive computer screen and each sector enlarges on screen when touched with a pointer or the operator's finger. The information provided in this grid system gives indication about the structure based upon quantitative measurements. Optionally, it provides qualitative analysis, such as indication of disease, severity of symptoms and/or prognosis.

Optionally, display 912 provides a chart such as chart 530. Such a chart provides a summary list of significant findings and/or an indication of disease. The information is shown on display 912 and printed by printout system 934.

While the invention has been described with respect to limited number of embodiments, it will be appreciated that many variations, modifications and other applications of the invention may be made. Also, elements from different embodiments may be provide din a single embodiment or a plurality of elements may be provided as a single elements may be used. Any and all such variations and modifications, as well as others that may become apparent to those skilled in the art are intended to be included within the scope of the invention, as defined by the appended claims.

The terms "include", "comprise" and "have" and their conjugates as used herein mean "including but not necessarily limited to."

It will be appreciated by a person skilled in the art that the present invention is not limited by what has thus far been described. Rather, the scope of the present invention is limited only by the following claims.

The invention claimed is:

1. A method of assessing condition of a skeletal joint comprising cartilage contiguous with bone and soft tissue in the joint, the method comprising:
   generating an ultrasound image comprising image pixels of the joint;
   generating a measure of the sharpness of an interface between the cartilage and soft tissue and/or bone responsive to the image; and
   using the sharpness measure to assess condition of the joint.

2. A method according to claim 1 and further comprising generating a measure of the brightness of a region of the image and using the brightness measure to assess condition of the joint.

3. A method according to claim 2 wherein the brightness measure is determined for a region of cartilage.

4. A method according to claim 3 wherein assessing the condition of the joint comprises determining that the cartilage is relatively healthy if the brightness measure indicates that the region is relatively dark.

5. A method according to claim 3 wherein assessing the condition of the joint comprises determining that the cartilage is damaged if the brightness measure indicates that the region is relatively bright.

6. A method according to claim 2 wherein the brightness measure is determined for a region of bone.

7. A method according to claim 6 wherein assessing the condition of the joint comprises determining that the bone is relatively healthy if the brightness measure indicates that the region is relatively bright.

8. A method according to claim 6 wherein assessing the condition of the joint comprises determining that the bone is damaged if the brightness measure indicates that the region brightness is relatively low.

9. A method according to claim 1 wherein generating a sharpness measure comprises:
   defining a plurality of substantially parallel lines in the image;
   determining a value for brightness for each line responsive to brightness of pixels along the line; and
   using the determined brightness values to generate the measure.

10. A method according to claim 9 wherein determining a value for the brightness value for a line comprises determining is an average of brightness of a plurality of pixels along the line.

11. A method according to claim 10 wherein determining a plurality of substantially parallel lines comprises defining at least some of the lines substantially parallel to the interface.

12. A method according to claim 11 wherein generating the measure of sharpness comprises determining a rate of change of line brightness as a function of line location for line locations associated with the neighborhood of the interface and using the rate of change to generate the sharpness measure.

13. A method according to claim 12 and determining that the sharpness measure indicates that the interface is relatively sharp if the rate of change is relatively high.

14. A method according to claim 12 and determining that the sharpness measure indicates that the interface is not relatively sharp if the rate of change is relatively low.

15. A method according to claim 1 and wherein assessing the condition of the joint comprises determining that tissue adjoining the interface is relatively healthy if the sharpness measure indicates that the interface is relatively sharp.

16. A method according to claim 1 wherein assessing the condition of the joint comprises determining that tissue adjoining the interface is damaged if the sharpness measure indicates that the interface is not relatively sharp.

17. A method according to claim 1 wherein the image is a B-scan image.

18. A method according to claim 2 wherein the joint is a human joint.

19. A method according to claim 2 wherein the joint is an equine joint.

20. A method of assessing condition of a skeletal joint comprising cartilage contiguous with bone and soft tissue in the joint, the method comprising:
   generating an ultrasound image comprising image pixels of the joint;
   defining a plurality of substantially parallel lines in the image;
   determining a value for brightness for each line responsive to brightness of pixels along the line; and
   using the determined brightness values to determine condition of the joint.

21. A method according to claim 20 wherein determining a brightness value for each line comprises determining an average brightness of a plurality of pixels along the line.

22. A method according to claim 20 wherein generating an ultrasound image comprises generating a B-scan image.

23. A method according to claim 20 wherein using brightness comprises determining whether an anomalous brightness exists in the image.

24. A method according to claim 23 wherein determining whether an anomalous brightness exists comprises determining whether an anomalously high brightness exists.

25. A method according to claim 24 wherein assessing the condition of the joint comprises determining that the cartilage is damaged if the anomalously high brightness is associated with locations in the cartilage.

26. A method according to claim 23 wherein determining whether an anomalous brightness exists comprises determining whether an anomalously low brightness exists.

27. A method according to claim 26 wherein assessing the condition of the joint comprises determining that bone is damaged if the anomalously low brightness is associated with locations in the bone.

28. A method according to claim 23 wherein using brightness comprises determining whether an anomalous brightness extends over a relatively large number of lines.

29. A method according to claim 28 wherein assessing the condition of the joint comprises determining that the cartilage is damaged if the anomalous brightness extends over a relatively large number of line locations.

30. A method according to claim 20 wherein using brightness comprises determining an average of the brightness values for a region of the joint through which a plurality of the lines pass and using the average to assess joint condition.

31. A method according to claim 30 wherein defining the lines comprises defining the lines so that the region comprises a region of cartilage in the joint.

32. A method according to claim 31 wherein assessing the condition of the joint comprises determining that the cartilage is damaged if the average brightness is relatively high.

33. A method according to claim 32 wherein defining the lines comprises defining the lines so that the region comprises a region of bone in the joint.

34. A method according to claim 33 wherein assessing the condition of the joint comprises determining that the bone is damaged if the average brightness is relatively low.

35. A method according to claim 20 wherein defining the lines comprises defining the lines so that at least some of the lines are substantially parallel to an interface between the cartilage and bone and/or soft tissue in the joint.

36. A method according to claim 35 wherein using brightness comprises determining a rate of change of brightness as a function of line location.

37. A method according to claim 36 wherein determining the rate of change comprises determining the rate of change for line locations associated with the neighborhood of an interface.

38. A method according to claim 37 wherein assessing the condition of the joint comprises determining that tissue adjoining the interface is relatively healthy if the rate of change is relatively high.

39. A method according to claim 37 wherein assessing the condition of the joint comprises determining that tissue adjoining the interface is damaged if the rate of change is relatively low.

40. A method according to claim 37 wherein assessing the condition of the joint comprises determining that tissue adjoining the interface is damaged if the rate of change is erratic.

41. A method according to claim 20 wherein using brightness comprises using a minimum value for brightness for line locations associated with the cartilage.

42. A method according to claim 20 wherein using brightness comprises using a maximum value for brightness for line locations associated with the bone.

43. A method according to claim 20 wherein using brightness comprises generating a value responsive to a rate of change in brightness as a function of line locations associated with a soft-tissue cartilage interface, a minimum value for brightness for line locations associated with the cartilage and a maximum value of brightness for line locations associated with the bone.

44. A method according to claim 43 and comprising determining the function to be a linear function of the rate of change, minimum and maximum brightness values.

45. A method according to claim 20 wherein the joint is a human joint.

46. A method according to claim 20 wherein the joint is an equine joint.

47. A method of assessing condition of a skeletal joint comprising cartilage contiguous with bone and soil tissue in the joint, the method comprising:
  generating an ultrasound image of the joint, which image comprises image pixels characterized by brightness values;
  determining a measure of rate of change in brightness of pixels as a function of distance for pixels that image a region of an interface between the cartilage and soft tissue and/or bone; and
  using the measure of rate of change to assess condition of the joint.

* * * * *